(12) United States Patent
Hage et al.

(10) Patent No.: US 6,610,641 B2
(45) Date of Patent: Aug. 26, 2003

(54) COMPOSITION AND METHOD FOR BLEACHING A SUBSTRATE

(75) Inventors: Ronald Hage, Vlaardingen (NL); Daniela Nühlen, Tubingen (DE); Thomas Weyhermüller, Mulheim (DE); Karl Wieghardt, Bochum (DE)

(73) Assignee: Unilever Home & Personal Care USA, division of Conopco, Inc., Greenwich, CT (US)

( * ) Notice: Subject to any disclaimer, the term of this patent is extended or adjusted under 35 U.S.C. 154(b) by 275 days.

(21) Appl. No.: 09/795,805

(22) Filed: Feb. 28, 2001

(65) Prior Publication Data

US 2002/0010120 A1 Jan. 24, 2002

(30) Foreign Application Priority Data

| Feb. 29, 2000 | (GB) | ............................................... 0004849 |
| Feb. 29, 2000 | (GB) | ............................................... 0004852 |
| Feb. 29, 2000 | (GB) | ............................................... 0004854 |

(51) Int. Cl.$^7$ ............................................... C11D 3/395
(52) U.S. Cl. ...................................... 510/375; 510/367
(58) Field of Search ................................... 510/367, 375

(56) References Cited

FOREIGN PATENT DOCUMENTS

| DE | 19714122 | 4/1997 |
| DE | 19721886 | 5/1997 |
| EP | 0 040 131 | 4/1981 |
| EP | 0 382 583 | 8/1990 |
| EP | 0 458 397 | 11/1991 |
| EP | 0 924 281 | 12/1997 |
| EP | 0 909 809 | 4/1999 |
| JP | 6256512 | 9/1994 |
| JP | 2000/034497 | 7/1998 |
| JP | 10-279411 | 10/1998 |
| WO | 90/12050 | 10/1990 |
| WO | 94/04485 | 3/1994 |
| WO | 95/19347 | 7/1995 |
| WO | 95/27772 | 10/1995 |
| WO | 95/28468 | 10/1995 |
| WO | 95/34628 | 12/1995 |
| WO | 96/06154 | 2/1996 |
| WO | 97/01360 | 1/1997 |
| WO | 97/07124 | 2/1997 |
| WO | 97/38074 | 10/1997 |
| WO | 97/48710 | 12/1997 |
| WO | 97/48787 | 12/1997 |
| WO | 00/12667 | 3/2000 |
| WO | 00/12808 | 3/2000 |

OTHER PUBLICATIONS

Abstract 119:236429.
Abstract129:269414.
J. Chem. Soc. No. 16, 1999, pp. 2751–2758.
J. Chem. Soc., No. 7, 1998, pp. 1085–1086.
J. Chem. Soc., No. 11, 1989, pp. 2079–2082.
J. Chem. Soc., No. 3, 1992, pp. 361–365.
Journal of Surfactants and Detergents, vol. 1, No. 2 (Apr. 1998), "Oxygen Bleaching Systems in Domestic Laundry" by Neil J. Milne, pp. 253–261.
Zhang et al. "Catalytic action of the iron(II) complexes of 8–methyl–1,4–bis(2–pyridylmethyl)–1,4m8–triazacycloundecane and 1–methyl–5,9–bis(2–pyridylmethyl)–1,5,9–triazacyclododecane" *J. Chem. Soc., Dalton Trans*, 1999, pp. 2751–2758.
De Martino Norante et al. "Transition metal complexes of a functionalized triazamacrocycle", *J. Chem. Soc., Dalton Trans*, 1992, pp. 361–365; (XP–002161048).

*Primary Examiner*—Yogendra N. Gupta
*Assistant Examiner*—John M Petruncio
(74) *Attorney, Agent, or Firm*—Milton L. Honig

(57) ABSTRACT

The invention relates to catalytically bleaching substrates, especially laundry fabrics, with a bleaching composition and a peroxyl source.

22 Claims, No Drawings

COMPOSITION AND METHOD FOR BLEACHING A SUBSTRATE

FIELD OF INVENTION

This invention relates to compositions and methods for catalytically bleaching substrates with a peroxyl species using a defined class of ligand or complex as catalyst.

BACKGROUND OF INVENTION

Peroxygen bleaches are well known for their ability to remove stains from substrates. Traditionally, the substrate is subjected to hydrogen peroxide, or to substances that can generate hydroperoxyl radicals, such as inorganic or organic peroxides. Generally, these systems must be activated. One method of activation is to employ wash temperatures of 60° C. or higher. However, these high temperatures often lead to inefficient cleaning, and can also cause premature damage to the substrate.

A preferred approach to generating hydroperoxyl bleach radicals is the use of inorganic peroxides coupled with organic precursor compounds. These systems are employed for many commercial laundry powders. For example, various European systems are based on tetraacetyl ethylenediamine (TAED) as the organic precursor coupled with sodium perborate or sodium percarbonate, whereas in the United States laundry bleach products are typically based on sodium nonanoyloxybenzenesulphonate (SNOBS) as the organic precursor coupled with sodium perborate.

Precursor systems are generally effective but still exhibit several disadvantages. For example, organic precursors are moderately sophisticated molecules requiring multi-step manufacturing processes resulting in high capital costs. Also, precursor systems have large formulation space requirements so that a significant proportion of a laundry powder must be devoted to the bleach components, leaving less room for other active ingredients and complicating the development of concentrated powders. Moreover, precursor systems do not bleach very efficiently in countries where consumers have wash habits entailing low dosage, short wash times, cold temperatures and low wash liquor to substrate ratios.

It is an object of the present invention to provide an effective bleaching system that functions satisfactorily in the absence or reduced amounts of organic precursor compounds found in commercial laundry products.

SUMMARY OF INVENTION

We have found that a selected class of ligand or complex is surprisingly effective in catalysing the bleaching of substrates using peroxyl species.

Accordingly, the present invention provides a composition comprising a ligand that forms a complex with a transition metal together with at least 1%, preferably at least 5%, of a peroxyl species or equivalent source thereof, wherein the ligand forms a complex of the general formula (A1):

$$[M_a L_k X_n] Y_m \quad (A1)$$

in which:
M represents a metal selected from Mn(II)–(III)–(IV)–(V), Cu(I)–(II)–(III), Fe(II)–(III)–(IV)–(V), Co(I)–(II)–(III), Ti(II)–(III)–(IV), V(II)–(III)–(IV)–(V), Mo(II)–(III)–(IV)–(V)–(VI) and W(IV)–(V)–(VI);
X represents a coordinating species selected from any mono, bi or tri charged anions and any neutral molecules able to coordinate the metal in a mono, bi or tridentate manner;
Y represents any non-coordinated counter ion;
a represents an integer from 1 to 10;
k represents an integer from 1 to 10;
n represents an integer from 1 to 10;
m represents zero or an integer from 1 to 20; and
L represents a ligand of the general formula (I), or its protonated or deprotonated analogue:

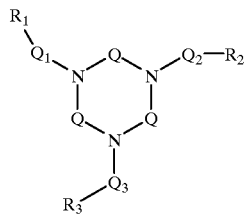

(I)

wherein
$R_1$, $R_2$, and $R_3$ independently represent a group selected from hydrogen, hydroxyl, halogen, —NH—C(NH)NH$_2$, —R and —OR, wherein R=alkyl, alkenyl, cycloalkyl, heterocycloalkyl, aryl, heteroaryl or a carbonyl derivative group, R being optionally substituted by one or more functional groups E;
Q independently represents a group selected from $C_{2-3}$-alkylene optionally substituted by H, benzyl or $C_{1-8}$-alkyl;
$Q_1$, $Q_2$ and $Q_3$ independently represent a group of the formula:

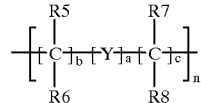

wherein
$5 \geq a+b+c \geq 1$; a=0–5; b=0–5; c=0–5; n=1 or 2;
Y independently represents a group selected from —O—, —S—, —SO—, —SO$_2$—, —C (O)—, arylene, alkylene, heteroarylene, heterocycloalkylene, —(G)P—, —P(O)— and —(G)N—, wherein G is selected from hydrogen, alkyl, aryl, arylalkyl, cycloalkyl, each except hydrogen being optionally substituted by one or more functional groups E;
R5, R6, R7, R8 independently represent a group selected from hydrogen, hydroxyl, halogen, —R and —OR, wherein R represents alkyl, alkenyl, cycloalkyl, heterocycloalkyl, aryl, heteroaryl or a carbonyl derivative group, R being optionally substituted by one or more functional groups E,
or R5 together with R6, or R7 together with R8, or both, represent oxygen,
or R5 together with R7 and/or independently R6 together with R8, or R5 together with R8 and/or independently R6 together with R7, represent $C_{1-6}$-alkylene optionally substituted by $C_{1-4}$-alkyl, —F, —Cl, —Br or —I; and
E independently represents a functional group selected from —F, —Cl, —Br, —I, —OH, —OR', —NH$_2$, —NHR', —N(R')$_2$, —N(R')$_3^+$, —C(O)R', —OC(O)R', —COOH, —COO$^-$(Na$^+$, K$^+$), —COOR', —C(O)NH$_2$, —C(O)NHR', —C(O)N(R')$_2$, heteroaryl, —R', —SR', —SH, —P(R')$_2$, —P(O)(R')$_2$, —P(O)(OH)$_2$, —P(O)(OR')$_2$, —NO$_2$, —SO$_3$H, —SO$_3^-$(Na$^+$, K$^+$), —S(O)$_2$R', —NHC(O)R', and —N(R')C(O)R', wherein R' represents cycloalkyl, aryl, arylalkyl, or alkyl optionally substituted by —F, —Cl, —Br, —I, —NH$_3^+$, —SO$_3$H, —SO$_3^-$(Na$^+$, K$^+$), —COOH, —COO$^-$(Na$^+$, K$^+$), —P(O)(OH)$_2$, or —P(O)(O$^-$(Na$^+$, K$^+$))$_2$, provided that at least one, preferably at least two, of R$_1$, R$_2$ and R$_3$ is a coordinating group.

A present invention also provides a method of bleaching a substrate comprising applying to the substrate, in an aqueous medium, a bleaching composition as defined herein.

The present invention also extends to use of a ligand or complex as defined below in the manufacture of a bleaching composition, the bleaching composition containing effective amounts of a peroxygen bleach or a peroxy-based or peroxy-generating bleach system. An effective amount of a peroxygen bleach may be provided by a composition containing at least 1%, preferably at least 5%, of a peroxyl species. In the present invention, it is preferred that the composition contains the range of about 1–35% by weight, preferably from 5–25% of a peroxyl species.

The present invention also extends to a commercial package comprising a bleaching composition according to the present invention together with instructions for its use.

DETAILED DESCRIPTION OF THE INVENTION

The ligand may be present as a preformed complex of a ligand and a transition metal. Alternatively, the composition may comprise a free ligand that complexes with a transition metal already present in the water or that complexes with a transition metal present in the substrate. The composition may also be formulated as a composition of a free ligand or a transition metal-substitutable metal-ligand complex, and a source of transition metal, whereby the complex is formed in situ in the medium.

The ligand forms a complex with one or more transition metals, in the latter case for example as a dinuclear complex. Suitable transition metals include for example: manganese in oxidation states II–V, iron II–V, copper I–III, cobalt I III, titanium II–IV, tungsten IV–VI, vanadium II–V and molybdenum II–VI.

At least two, and preferably at least three, of R$_1$, R$_2$ and R$_3$ independently represent a group selected from carboxylate, amido, —NH—C(NH)NH$_2$, hydroxyphenyl, an optionally substituted heterocyclic ring or an optionally substituted heteroaromatic ring selected from pyridine, pyrimidine, pyrazine, pyrazole, imidazole, benzimidazole, pyrrole, quinoline, quinoxaline, triazole, isoquinoline, carbazole, indole, isoindole, oxazole and thiazole. Preferably, at least two of R$_1$, R$_2$, R$_3$ each independently represent a coordinating group selected from optionally substituted pyridin-2-yl, optionally substituted imidazol-2-yl, optionally substituted imidazol-4-yl, optionally substituted pyrazol-1-yl, and optionally substituted quinolin-2-yl.

Preferably, substituents for groups R$_1$, R$_2$, R$_3$, when representing a heterocyclic or heteroaromatic ring, are selected from C$_{1-4}$-alkyl, aryl, arylalkyl, heteroaryl, methoxy, hydroxy, nitro, amino, carboxyl, halo, and carbonyl.

The groups R5, R6, R7, R8 preferably independently represent a group selected from —H, hydroxy-C$_0$–C$_{20}$-alkyl, halo-C$_0$–C$_{20}$-alkyl, nitroso, formyl-C$_0$–C$_{20}$-alkyl, carboxyl-C$_0$–C$_{20}$-alkyl and esters and salts thereof, carbamoyl-C$_0$–C$_{20}$-alkyl, sulpho-C$_0$–C$_{20}$-alkyl and esters and salts thereof, sulphamoyl-C$_0$–C$_{20}$-alkyl, amino-C$_0$–C$_{20}$-alkyl, aryl-C$_0$–C$_{20}$-alkyl, C$_0$–C$_{20}$-alkyl, alkoxy-C$_0$–C$_8$-alkyl, carbonyl-C$_0$–C$_6$-alkoxy, and C$_0$–C$_{20}$-alkylamide. Preferably, none of R6–R8 is linked together.

Preferably, Q$_1$, Q$_2$ and Q$_3$ are defined such that a=b=0, c=1,2,3 or 4 and n=1. Preferably, the groups Q$_1$, Q$_2$ and Q$_3$ independently represent a group selected from —CH$_2$— and —CH$_2$CH$_2$—.

Group Q is preferably a group selected from —CH$_2$CH$_2$— and —CH$_2$CH$_2$CH$_2$—.

In a first preferred embodiment, the ligand L is of the general formula (II):

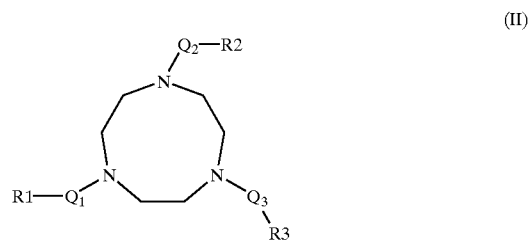

(II)

wherein R1, R2, R3 are as defined previously for R$_1$, R$_2$, R$_3$, and Q$_1$, Q$_2$, Q$_3$ are as defined previously.

Preferred classes of ligands according to the first preferred embodiment, as represented by formula (II) above, are as follows:

(i) ligands of the general formula (II) wherein:
R1, R2, R3 each independently represent a coordinating group selected from carboxylate, amido, —NH—C(NH)NH$_2$, hydroxyphenyl, an optionally substituted heterocyclic ring or an optionally substituted heteroaromatic ring selected from pyridine, pyrimidine, pyrazine, pyrazole, imidazole, -pyrrole, benzimidazole, quinoline, quinoxaline, triazole, isoquinoline, carbazole, indole, isoindole, oxazole and thiazole.

In this class, we prefer that:
R1, R2, R3 each independently represent a coordinating group selected from optionally substituted pyridin-2-yl, optionally substituted imidazol-2-yl, optionally substituted imidazol-4-yl, optionally substituted pyrazol-1-yl, and optionally substituted quinolin-2-yl.

(ii) ligands of the general formula (II) wherein:
two of R1, R2, R3 each independently represent a coordinating group selected from carboxylate, amido, —NH—C(NH) NH$_2$, hydroxyphenyl, an optionally substituted heterocyclic ring or an optionally substituted heteroaromatic ring selected from pyridine, pyrimidine, pyrazine, pyrazole, imidazole, benzimidazole, quinoline, quinoxaline, triazole, isoquinoline, carbazole, indole, isoindole, oxazole and thiazole; and one of R1, R2, R3 represents a group selected from hydrogen, C$_{1-20}$ optionally substituted alkyl, C$_{1-20}$ optionally substituted arylalkyl, aryl, and C$_{1-20}$ optionally substituted NR$_3^+$ (wherein R=C$_{1-8}$-alkyl).

In this class, we prefer that:
two of R1, R2, R3 each independently represent a coordinating group selected from optionally substituted pyridin-2-yl, optionally substituted imidazol- 2-yl, optionally substituted imidazol-4-yl, optionally substituted pyrazol-1-yl, and optionally substituted quinolin-2-yl; and one of R1, R2, R3 represents a group selected from hydrogen, $C_{1-10}$ optionally substituted alkyl, $C_{1-5}$-furanyl, $C_{1-5}$ optionally substituted benzylalkyl, benzyl, $C_{1-5}$ optionally substituted alkoxy, and $C_{1-20}$ optionally substituted $N^+Me_3$.

In especially preferred embodiments, the ligand L is selected from:

1,4,7-Tris(pyrazol-3-ylmethyl)-1,4,7-triazacyclononane; 1,4,7-Tris(pyrazol-1-ylmethyl)-1,4,7-triazacyclononane; 1-ethyl-4,7-bis(quinolin-2-ylmethyl)-1,4,7-triazacyclononane; 1,4-bis(pyridin-2-ylmethyl)-7-ethyl-1,4,7-triazacyclononane; 1,4-bis(pyrazol-1-ylmethyl)-7-ethyl-1,4,7-triazacyclononane; 1,4,7-Tris(benzimidazol-2-ylmethyl)-1,4,7-triazacyclononane; 1,4,7-tris(N-methyl-benzimidazol-2ylmethyl)-1,4,7-triazacyclononane; 1,4-bis(imidazol-2ylmethyl)-7-ethyl-1,4,7-triazacyclononane; 1,4,7-tris(4-bromo-pyrazol-3ylmethyl)-1,4,7-triazacyclononane; 1,4,7-tris(pyrrole-2ylmethyl)-1,4,7-triazacyclononane; 1,4-bis(quinolin-2-ylmethyl)-7-ethyl-1,4,7-triazacyclononane; 1,4-bis (pyrazol-1-ylmethyl)-7-ethyl-1,4,7-triazacyclononane; 1,4-bis(3,5-dimethylpyrazol-1-ylmethyl)-7-ethyl-1,4,7-triazacyclononane; 1,4-bis(N-methylimidazol-2-ylmethyl)-7-ethyl-1,4,7-triazacyclononane; 1,4,7-tris(quinolin-2-ylmethyl)-1,4,7-triazacyclononane; 1,4-bis(N-isopropylacetamido)-7-ethyl-1,4,7-triazacyclononane; and, 1,4-bis(N-methylacetamido)-7-ethyl-1,4,7-triazacyclononane.

The counter ions Y in formula (A1) balance the charge z on the complex formed by the ligand L, metal M and coordinating species X. Thus, if the charge z is positive, Y may be an anion such as $RCOO^-$, $BPh_4^-$, $ClO_4^-$, $BF_4^-$, $PF_6^-$, $RSO_3^-$, $RSO_4^-$, $SO_4^{2-}$, $NO_3^-$, $F^-$, $Cl^-$, $Br^-$, or $I^-$, with R being hydrogen, optionally substituted alkyl or optionally substituted aryl. If z is negative, Y may be a common cation such as an alkali metal, alkaline earth metal or (alkyl) ammonium cation.

Suitable counter ions Y include those which give rise to the formation of storage-stable solids. Preferred counter ions for the preferred metal complexes are selected from $R^7COO^-$, $ClO_4^-$, $BF_4^-$, $PF_6^-$, $RSO_3^-$ (in particular $CF_3SO_3^-$), $RSO_4^-$, $SO_4^{2-}$, $NO_3^-$, $F^-$, $Cl^-$, $Br^-$, and $I^-$, wherein R represents hydrogen or optionally substituted phenyl, naphthyl or $C_1$–$C_4$ alkyl.

It will be appreciated that the complex (A1) can be formed by any appropriate means, including in situ formation whereby precursors of the complex are transformed into the active complex of general formula (A1) under conditions of storage or use. Preferably, the complex is formed as a well-defined complex or in a solvent mixture comprising a salt of the metal M and the ligand L or ligand L-generating species. Alternatively, the catalyst may be formed in situ from suitable precursors for the complex, for example in a solution or dispersion containing the precursor materials. In one such example, the active catalyst may be formed in situ in a mixture comprising a salt of the metal M and the ligand L, or a ligand L-generating species, in a suitable solvent. Thus, for example, if M is iron, an iron salt such as $FeSO_4$ can be mixed in solution with the ligand L, or a ligand L-generating species, to form the active complex. Thus, for example, the composition may formed from a mixture of the ligand L and a metal salt $MX_n$ in which preferably n=1–5, more preferably 1–3. In another such example, the ligand L, or a ligand L-generating species, can be mixed with metal M ions present in the substrate or wash liquor to form the active catalyst in situ. Suitable ligand L-generating species include metal-free compounds or metal coordination complexes that comprise the ligand L and can be substituted by metal M ions to form the active complex according the formula (A1).

We have also found that this selected class of ligand or transition metal complexes thereof may be used as air bleaching catalysts as disclosed, in part, in the GB priority documents 0004849.6, 0004852.0, and 0004854.6. The peroxyl concentration present in a composition of the present invention is such that substantially no air bleaching takes place. Thus, at least at least 90% of any bleaching of the substrate is effected by a peroxyl species not derived directly from atmospheric oxygen, preferably 99% and most preferably 100%.

The bleaching compositions according to the present invention may be used for laundry cleaning, hard surface cleaning (including cleaning of lavatories, kitchen work surfaces, floors, mechanical ware washing etc.). As is generally known in the art, bleaching compositions are also employed in waste-water treatment, pulp bleaching during the manufacture of paper, leather manufacture, dye transfer inhibition, food processing, starch bleaching, sterilisation, whitening in oral hygiene preparations and/or contact lens disinfection.

In the context of the present invention bleaching should be understood as relating generally to the decolourisation of stains or of other materials attached to or associated with a substrate. However, it is envisaged that the present invention can be applied where a requirement is the removal and/or neutralisation by an oxidative bleaching reaction of malodours or other undesirable components attached to or otherwise associated with a substrate.

In typical washing compositions the level of the catalyst is such that the in-use level is from 1 $\mu$M to 50 mM, with preferred in-use levels for domestic laundry operations falling in the range 10 to 100 $\mu$M. Higher levels may be desired and applied in industrial bleaching processes, such as textile and paper pulp bleaching.

Preferably, the aqueous medium has a pH in the range from pH 6 to 13, more preferably from pH 6 to 11, still more preferably from pH 8 to 11, and most preferably from pH 8 to 10, in particular from pH 9 to 10.

The Peroxy Species or Precursor Thereof

The peroxy bleaching species may be a compound which is capable of yielding hydrogen peroxide in aqueous solution. Hydrogen peroxide sources are well known in the art. They include the alkali metal peroxides, organic peroxides such as urea peroxide, and inorganic persalts, such as the alkali metal perborates, percarbonates, perphosphates persilicates and persulphates. Mixtures of two or more such compounds may also be suitable.

Particularly preferred are sodium perborate tetrahydrate and, especially, sodium perborate monohydrate. Sodium perborate monohydrate is preferred because of its high active oxygen content. Sodium percarbonate may also be preferred for environmental reasons. The amount thereof in the composition of the invention usually will be within the range of about 1–35% by weight, preferably from 5–25% by weight. One skilled in the art will appreciate that these amounts may be reduced in the presence of a bleach precursor e.g., N,N,N'N'-tetraacetyl ethylene diamine (TAED).

Another suitable hydrogen peroxide generating system is a combination of a C1–C4 alkanol oxidase and a C1–C4 alkanol, especially a combination of methanol oxidase (MOX) and ethanol. Such combinations are disclosed in International Application PCT/EP 94/03003 (Unilever), which is incorporated herein by reference.

Alkylhydroxy peroxides are another class of peroxy bleaching compounds. Examples of these materials include cumene hydroperoxide and t-butyl hydroperoxide.

Organic peroxyacids may also be suitable as the peroxy bleaching compound. Such materials normally have the general formula:

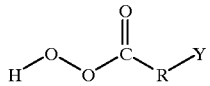

wherein R is an alkylene or substituted alkylene group containing from 1 to about 20 carbon atoms, optionally having an internal amide linkage; or a phenylene or substituted phenylene group; and Y is hydrogen, halogen, alkyl, aryl, an imido-aromatic or non-aromatic group, a COOH or

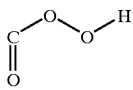

group or a quaternary ammonium group.

Typical monoperoxy acids useful herein include, for example:
(i) peroxybenzoic acid and ring-substituted peroxybenzoic acids, e.g. peroxy-.alpha.-naphthoic acid;
(ii) aliphatic, substituted aliphatic and arylalkyl monoperoxyacids, e.g. peroxylauric acid, peroxystearic acid and N,N-phthaloylaminoperoxy caproic acid (PAP); and
(iii) 6-octylamino-6-oxo-peroxyhexanoic acid.

Typical diperoxyacids useful herein include, for example:
(iv) 1,12-diperoxydodecanedioic acid (DPDA);
(v) 1,9-diperoxyazelaic acid;
(vi) diperoxybrassilic acid; diperoxysebasic acid and diperoxyisophthalic acid;
(vii) 2-decyldiperoxybutane-1,4-diotic acid; and
(viii) 4,4'-sulphonylbisperoxybenzoic acid.

Also inorganic peroxyacid compounds are suitable, such as for example potassium monopersulphate (MPS). If organic or inorganic peroxyacids are used as the peroxygen compound, the amount thereof will normally be within the range of about 2–10% by weight, preferably from 4–8% by weight.

Peroxyacid bleach precursors are known and amply described in literature, such as in the British Patents 836988; 864,798; 907,356; 1,003,310 and 1,519,351; German Patent 3,337,921; EP-A-0185522; EP-A-0174132; EP-A-0120591; and U.S. Pat. Nos. 1,246,339; 3,332,882; 4,128,494; 4,412,934 and 4,675,393.

Another useful class of peroxyacid bleach precursors is that of the cationic i.e. quaternary ammonium substituted peroxyacid precursors as disclosed in U.S. Pat. Nos. 4,751,015 and 4,397,757, in EP-A0284292 and EP-A-331,229. Examples of peroxyacid bleach precursors of this class are:
2-(N,N,N-trimethyl ammonium) ethyl sodium-4-sulphonphenyl carbonate chloride (SPCC);
N-octyl-N,N-dimethyl-N10-carbophenoxy decyl ammonium chloride (ODC);
3-(N,N,N-trimethyl ammonium) propyl sodium-4-sulphophenyl carboxylate; and
N,N,N-trimethyl ammonium toluyloxy benzene sulphonate.

A further special class of bleach precursors is formed by the cationic nitriles as disclosed in EP-A-303,520 and in European Patent Specification No.'s 458,396 and 464,880.

Any one of these peroxyacid bleach precursors can be used in the present invention, though some may be more preferred than others.

Of the above classes of bleach precursors, the preferred classes are the esters, including acyl phenol sulphonates and acyl alkyl phenol sulphonates; the acyl-amides; and the quaternary ammonium substituted peroxyacid precursors including the cationic nitriles.

Examples of said preferred peroxyacid bleach precursors or activators are sodium-4-benzoyloxy benzene sulphonate (SBOBS); N,N,N'N'-tetraacetyl ethylene diamine (TAED); sodium-1-methyl-2-benzoyloxy benzene-4-sulphonate; sodium-4-methyl-3-benzoloxy benzoate; SPCC; trimethyl ammonium toluyloxy-benzene sulphonate; sodium nonanoyloxybenzene sulphonate (SNOBS); sodium 3,5,5-trimethyl hexanoyl-oxybenzene sulphonate (STHOBS); and the substituted cationic nitriles.

The precursors may be used in an amount of up to 12%, preferably from 2–10% by weight, of the composition.

The bleaching composition of the present invention has particular application in detergent formulations, especially for laundry cleaning. Accordingly, in another preferred embodiment, the present invention provides a detergent bleach composition comprising a bleaching composition as defined above and additionally a surface-active material, optionally together with detergency builder.

The bleach composition according to the present invention may for example contain a surface-active material in an amount of from 10 to 50% by weight. The surface-active material may be naturally derived, such as soap, or a synthetic material selected from anionic, nonionic, amphoteric, zwitterionic, cationic actives and mixtures thereof. Many suitable actives are commercially available and are fully described in the literature, for example in "Surface Active Agents and Detergents", Volumes I and II, by Schwartz, Perry and Berch.

Typical synthetic anionic surface-actives are usually water-soluble alkali metal salts of organic sulphates and sulphonates having alkyl groups containing from about 8 to about 22 carbon atoms, the term "alkyl" being used to include the alkyl portion of higher aryl groups. Examples of suitable synthetic anionic detergent compounds are sodium and ammonium alkyl sulphates, especially those obtained by sulphating higher ($C_8$–$C_{18}$) alcohols produced, for example, from tallow or coconut oil; sodium and ammonium alkyl ($C_9$–$C_{20}$) benzene sulphonates, particularly sodium linear secondary alkyl ($C_{10}$–$C_{15}$) benzene sulphonates; sodium alkyl glyceryl ether sulphates, especially those ethers of the higher alcohols derived from tallow or coconut oil fatty acid monoglyceride sulphates and sulphonates; sodium and ammonium salts of sulphuric acid esters of higher ($C_9$–$C_{18}$) fatty alcohol alkylene oxide, particularly ethylene oxide, reaction products; the reaction products of fatty acids such as coconut fatty acids esterified with isethionic acid and neutralised with sodium hydroxide; sodium and ammonium salts of fatty acid amides of methyl taurine; alkane monosulphonates such as those derived by reacting alpha-olefins ($C_8$–$C_{20}$) with sodium bisulphite and those derived by reacting paraffins with $SO_2$ and $Cl_2$ and then hydrolysing with a base to produce a random sulphonate; sodium and ammonium ($C_7$–$C_{12}$) dialkyl sulphosuccinates; and olefin sulphonates, which term is used to describe material made by reacting olefins, particularly ($C_{10}$–$C_{20}$) alpha-olefins, with $SO_3$ and then neutralising and hydrolysing the reaction product. The preferred anionic detergent compounds are sodium ($C_{10}$–$C_{15}$) alkylbenzene sulphonates, and sodium ($C_{16}$–$C_{18}$) alkyl ether sulphates.

Examples of suitable nonionic surface-active compounds which may be used, preferably together with the anionic surface-active compounds, include, in particular, the reaction products of alkylene oxides, usually ethylene oxide, with alkyl ($C_6$–$C_{22}$) phenols, generally 5–25 EO, i.e. 5–25 units of ethylene oxides per molecule; and the condensation products of aliphatic ($C_8$–$C_{18}$) primary or secondary linear or branched alcohols with ethylene oxide, generally 2–30 EO. Other so-called nonionic surface-actives include alkyl polyglycosides, sugar esters, long-chain tertiary amine oxides, long-chain tertiary phosphine oxides and dialkyl sulphoxides.

Amphoteric or zwitterionic surface-active compounds can also be used in the compositions of the invention but this is not normally desired owing to their relatively high cost. If any amphoteric or zwitterionic detergent compounds are used, it is generally in small amounts in compositions based on the much more commonly used synthetic anionic and nonionic actives.

The detergent bleach composition of the invention will preferably comprise from 1 to 15% wt of anionic surfactant and from 10 to 40% by weight of nonionic surfactant. In a further preferred embodiment, the detergent active system is free from $C_{16}$–$C_{12}$ fatty acid soaps.

The bleach composition of the present invention may also contain a detergency builder, for example in an amount of from about 5 to 80% by weight, preferably from about 10 to 60% by weight.

Builder materials may be selected from 1) calcium sequestrant materials, 2) precipitating materials, 3) calcium ion-exchange materials and 4) mixtures thereof.

Examples of calcium sequestrant builder materials include alkali metal polyphosphates, such as sodium tripolyphosphate; nitrilotriacetic acid and its water-soluble salts; the alkali metal salts of carboxymethyloxy succinic acid, ethylene diamine tetraacetic acid, oxydisuccinic acid, mellitic acid, benzene polycarboxylic acids, citric acid; and polyacetal carboxylates as disclosed in U.S. Pat. No. 4,144,226 and U.S. Pat. No. 4,146,495.

Examples of precipitating builder materials include sodium orthophosphate and sodium carbonate.

Examples of calcium ion-exchange builder materials include the various types of water-insoluble crystalline or amorphous aluminosilicates, of which zeolites are the best known representatives, e.g. zeolite A, zeolite B (also known as zeolite P), zeolite C, zeolite X, zeolite Y and also the zeolite P-type as described in EP-A-0,384,070.

In particular, the compositions of the invention may contain any one of the organic and inorganic builder materials, though, for environmental reasons, phosphate builders are preferably omitted or only used in very small amounts. Typical builders usable in the present invention are, for example, sodium carbonate, calcite/carbonate, the sodium salt of nitrilotriacetic acid, sodium citrate, carboxymethyloxy malonate, carboxymethyloxy succinate and water-insoluble crystalline or amorphous aluminosilicate builder materials, each of which can be used as the main builder, either alone or in admixture with minor amounts of other builders or polymers as co-builder.

It is preferred that the composition contains not more than 5% by weight of a carbonate builder, expressed as sodium carbonate, more preferably not more than 2.5% by weight to substantially nil, if the composition pH lies in the lower alkaline region of up to 10.

Apart from the components already mentioned, the bleach composition of the present invention can contain any of the conventional additives in amounts of which such materials are normally employed in fabric washing detergent compositions. Examples of these additives include buffers such as carbonates, lather boosters, such as alkanolamides, particularly the monoethanol amides derived from palmkernel fatty acids and coconut fatty acids; lather depressants, such as alkyl phosphates and silicones; anti-redeposition agents, such as sodium carboxymethyl cellulose and alkyl or substituted alkyl cellulose ethers; stabilisers, such as phosphonic acid derivatives (i.e. Dequest® types); fabric softening agents; inorganic salts and alkaline buffering agents, such as sodium sulphate and sodium silicate; and, usually in very small amounts, fluorescent agents; perfumes; enzymes, such as proteases, cellulases, lipases, amylases and oxidases; germicides and colourants.

Transition metal sequestrants such as EDTA, and phosphonic acid derivatives such as EDTMP (ethylene diamine tetra(methylene phosphonate)) may also be included, in addition to the ligand specified, for example to improve the stability sensitive ingredients such as enzymes, fluorescent agents and perfumes, but provided the composition remains bleaching effective.

In a particularly preferred embodiment the method of the present invention is carried out on a laundry fabric using aqueous treatment liquor. In particular the treatment may be effected in, or as an adjunct to, an essentially conventional wash cycle for cleaning laundry. More preferably, the treatment is carried out in an aqueous detergent wash liquor. The bleaching composition can be delivered into the wash liquor from a powder, granule, pellet, tablet, block, bar or other such solid form. The solid form can comprise a carrier, which can be particulate, sheet-like or comprise a three-dimensional object. The carrier can be dispersible or soluble in the wash liquor or may remain substantially intact. In other embodiments, the bleaching composition can be delivered into the wash liquor from a paste, gel or liquid concentrate. Other means for ensuring that the bleaching composition is present in the wash liquor may be envisaged.

For example, it is envisaged that the bleaching composition can be presented in the form of a body from which it is slowly released during the whole or part of the laundry process. Such release can occur over the course of a single wash or over the course of a plurality of washes. In the latter case it is envisaged that the bleaching composition can be released from a carrier substrate used in association with the wash process, e.g. from a body placed in the dispenser drawer of a washing machine, elsewhere in the delivery system or in the drum of the washing machine. When used in the drum of the washing machine the carrier can be freely moving or fixed relative to the drum. Such fixing can be achieved by mechanical means, for example by barbs that interact with the drum wall, or employ other forces, for example a magnetic force. The modification of a washing machine to provide for means to hold and retain such a carrier is envisaged similar means being known from the analogous art of toilet block manufacture. Freely moving carriers such as shuttles for dosage of surfactant materials and/or other detergent ingredients into the wash can comprise means for the release of the bleaching composition into the wash.

The present invention is not limited to those circumstances in which a washing machine is employed, but can be applied where washing is performed in some alternative vessel. In these circumstances it is envisaged that the bleaching composition can be delivered by means of slow release from the bowl, bucket or other vessel which is being employed, or from any implement which is being employed, such as a brush, bat or dolly, or from any suitable applicator.

Suitable pre-treatment means for application of the bleaching composition to the textile material prior to the main wash include sprays, pens, roller-ball devices, bars, soft solid applicator sticks and impregnated cloths or cloths containing microcapsules. Such means are well known in the analogous art of deodorant application and/or in spot treatment of textiles. Similar means for application are employed in those embodiments where the bleaching composition is applied after the main washing and/or conditioning steps have been performed, e.g. prior to or after ironing or drying of the cloth. For example, the bleaching composition may be applied using tapes, sheets or sticking plasters coated or impregnated with the substance, or containing microcapsules of the substance. The bleaching composition may for example be incorporated into a drier sheet so as to be activated or released during a tumble-drier cycle, or the substance can be provided in an impregnated or microcapsule-containing sheet so as to be delivered to the textile when ironed.

Throughout the description and claims generic groups have been used, for example alkyl, alkoxy, aryl. Unless otherwise specified the following are preferred group restrictions that may be applied to generic groups found within compounds disclosed herein:

alkyl: linear and branched C1–C8-alkyl,
alkenyl: C2–C6-alkenyl,
cycloalkyl: C3–C8-cycloalkyl,
alkoxy: C1–C6-alkoxy,
alkylene: selected from the group consisting of: methylene; 1,1-ethylene; 1,2-ethylene; 1,1-propylidene; 1,2-propylene; 1,3-propylene; 2,2-propylidene; butan-2-ol-1,4-diyl; propan-2-ol-1,3-diyl; 1,4-butylene; cyclohexane-1,1-diyl; cyclohexan-1,2-diyl; cyclohexan-1,3-diyl; cyclohexan-1,4-diyl; cyclopentane-1,1-diyl; cyclopentan-1,2-diyl; and cyclopentan-1,3-diyl,
aryl: selected from homoaromatic compounds having a molecular weight under 300,
arylene: selected from the group consisting of: 1,2-phenylene; 1,3-phenylene; 1,4-phenylene; 1,2-naphtalenylene; 1,3-naphtalenylene; 1,4-naphtalenylene; 2,3-naphtalenylene; 1-hydroxy-2,3-phenylene; 1-hydroxy-2,4-phenylene; 1-hydroxy-2,5-phenylene; and 1-hydroxy-2,6-phenylene,
heteroaryl: selected from the group consisting of: pyridinyl; pyrimidinyl; pyrazinyl; triazolyl; pyridazinyl; 1,3,5-triazinyl; quinolinyl; isoquinolinyl; quinoxalinyl; imidazolyl; pyrazolyl; benzimidazolyl; thiazolyl; oxazolidinyl; pyrrolyl; carbazolyl; indolyl; and isoindolyl, wherein the heteroaryl may be connected to the compound via any atom in the ring of the selected heteroaryl,
heteroarylene: selected from the group consisting of: pyridindiyl; quinolindiyl; pyrazodiyl; pyrazoldiyl; triazolediyl; pyrazindiyl; and imidazolediyl, wherein the heteroarylene acts as a bridge in the compound via any atom in the ring of the selected heteroarylene, more specifically preferred are: pyridin-2,3-diyl; pyridin-2,4-diyl; pyridin-2,5-diyl; pyridin-2,6-diyl; pyridin-3,4-diyl; pyridin-3,5-diyl; quinolin-2,3-diyl; quinolin-2,4-diyl; quinolin-2,8-diyl; isoquinolin-1,3-diyl; isoquinolin-1,4-diyl; pyrazol-1,3-diyl; pyrazol-3,5-diyl; triazole-3,5-diyl; triazole-1,3-diyl; pyrazin-2,5-diyl; and imidazole-2,4-diyl,
heterocycloalkyl: selected from the group consisting of: pyrrolinyl; pyrrolidinyl; morpholinyl; piperidinyl; piperazinyl; hexamethylene imine; 1,4-piperazinyl; tetrahydrothiophenyl; tetrahydrofuranyl; 1,4,7-triazacyclononanyl; 1,4,8,11-tetraazacyclotetradecanyl; 1,4,7,10,13-pentaazacyclopentadecanyl; 1,4-diaza-7-thia-cyclononanyl; 1,4-diaza-7-oxa-cyclononanyl; 1,4,7,10-tetraazacyclododecanyl; 1,4-dioxanyl; 1,4,7-trithia-cyclononanyl; tetrahydropyranyl; and oxazolidinyl, wherein the heterocycloalkyl may be connected to the compound via any atom in the ring of the selected heterocycloalkyl,
heterocycloalkylene: selected from the group consisting of: piperidin-1,2-ylene; piperidin-2,6-ylene; piperidin-4,4-ylidene; 1,4-piperazin-1,4-ylene; 1,4-piperazin-2,3-ylene; 1,4-piperazin-2,5-ylene; 1,4-piperazin-2,6-ylene; 1,4-piperazin-1,2-ylene; 1,4-piperazin-1,3-ylene; 1,4-piperazin-1,4-ylene; tetrahydrothiophen-2,5-ylene; tetrahydrothiophen-3,4-ylene; tetrahydrothiophen-2,3-ylene; tetrahydrofuran-2,5-ylene; tetrahydrofuran-3,4-ylene; tetrahydrofuran-2,3-ylene; pyrrolidin-2,5-ylene; pyrrolidin-3,4-ylene; pyrrolidin-2,3-ylene; pyrrolidin-1,2-ylene; pyrrolidin-1,3-ylene; pyrrolidin-2,2-ylidene; 1,4,7-triazacyclonon-1,4-ylene; 1,4,7-triazacyclonon-2,3-ylene; 1,4,7-triazacyclonon-2,9-ylene; 1,4,7-triazacyclonon-3,8-ylene; 1,4,7-triazacyclonon-2,2-ylidene; 1,4,8,11-tetraazacyclotetradec-1,4-ylene; 1,4,8,11-tetraazacyclotetradec-1,8-ylene; 1,4,8,11-tetraazacyclotetradec-2,3-ylene; 1,4,8,11-tetraazacyclotetradec-2,5-ylene; 1,4,8,11-tetraazacyclotetradec-1,2-ylene; 1,4,8,11-tetraazacyclotetradec-2,2-ylidene; 1,4,7,10-tetraazacyclododec-1,4-ylene; 1,4,7,10-tetraazacyclododec-1,7-ylene; 1,4,7,10-tetraazacyclododec-1,2-ylene; 1,4,7,10-tetraazacyclododec-2,3-ylene; 1,4,7,10-tetraazacyclododec-2,2-ylidene; 1,4,7,10,13-pentaazacyclopentadec-1,4-ylene; 1,4,7,10,13-pentaazacyclopentadec-1,7-ylene; 1,4,7,10,13-pentaazacyclopentadec-2,3-ylene; 1,4,7,10,13-pentaazacyclopentadec-1,2-ylene; 1,4,7,10,13-pentaazacyclopentadec-2,2-ylidene; 1,4-diaza-7-thia-cyclonon-1,4-ylene; 1,4-diaza-7-thia-cyclonon-1,2-ylene; 1,4-diaza-7-thia-cyclonon-2,3-ylene; 1,4-diaza-7-thia-cyclonon-6,8-ylene; 1,4-diaza-7-thia-cyclonon-2,2-ylidene; 1,4-diaza-7-oxa-cyclonon-1,4-ylene; 1,4-diaza-7-oxa-cyclonon-1,2-ylene; 1,4-diaza-7-oxa-cyclonon-2,3-ylene; 1,4-diaza-7-oxa-cyclonon-6,8-ylene; 1,4-diaza-7-oxa-cyclonon-2,2-ylidene; 1,4-dioxan-2,3-ylene; 1,4-dioxan-2,6-ylene; 1,4-dioxan-2,2-ylidene; tetrahydropyran-2,3-ylene; tetrahydropyran-2,6-ylene; tetrahydropyran-2,5-ylene; tetrahydropyran-2,2-ylidene; 1,4,7-trithia-cyclonon-2,3-ylene; 1,4,7-trithia-cyclonon-2,9-ylene; and 1,4,7-trithia-cyclonon-2,2-ylidene,
amine: the group —N(R)$_2$ wherein each R is independently selected from: hydrogen; C1–C6-alkyl; C1–C6-alkyl-C6H5; and phenyl, wherein when both R are C1–C6-alkyl both R together may form an —NC3 to an —NC5 heterocyclic ring with any remaining alkyl chain forming an alkyl substituent to the heterocyclic ring,
halogen: selected from the group consisting of: F; Cl; Br and I,
sulphonate: the group —S(O)$_2$OR, wherein R is selected from: hydrogen; C1–C6-alkyl; phenyl; C1–C6-alkyl-C6H5; Li; Na; K; Cs; Mg; and Ca,
sulphate: the group —OS(O)$_2$OR, wherein R is selected from: hydrogen; C1–C6-alkyl; phenyl; C1–C6-alkyl-C6H5; Li; Na; K; Cs; Mg; and Ca,
sulphone: the group —S(O)$_2$R, wherein R is selected from: hydrogen; C1–C6-alkyl; phenyl; C1–C6-alkyl-C6H5 and amine (to give sulphonamide) selected from the group: —NR'2, wherein each R' is independently selected from: hydrogen; C1–C6-alkyl; C1–C6-alkyl-C6H5; and phenyl, wherein when both R' are C1–C6-alkyl both R' together may form an —NC3 to an —NC5 heterocyclic ring with any remaining alkyl chain forming an alkyl substituent to the heterocyclic ring, carboxylate derivative: the group —C(O)OR, wherein R is selected from: hydrogen; C1–C6-alkyl; phenyl; C1–C6-alkyl-C6H5; Li; Na; K; Cs; Mg; and Ca, carbonyl derivative: the group —C(O)R, wherein R is selected from: hydrogen; C1–C6-alkyl; phenyl; C1–C6-alkyl-C6H5 and amine (to give amide) selected from the group: —NR'2, wherein each R' is independently selected from: hydrogen; C1–C6-alkyl; C1–C6-alkyl-C6H5; and phenyl, wherein when both R' are C1–C6-alkyl both R' together may form an —NC3 to an —NC5 heterocyclic ring with any remaining alkyl chain forming an alkyl substituent to the heterocyclic ring, phosphonate: the group —P(O)(OR)$_2$, wherein each R is independently selected from: hydrogen; C1–C6-alkyl; phenyl; C1–C6-alkyl-C6H5; Li; Na; K; Cs; Mg; and Ca, phosphate: the group —OP(O)(OR)$_2$, wherein each R is independently selected from: hydrogen; C1–C6-alkyl; phenyl; C1–C6-alkyl-C6H5; Li; Na; K; Cs; Mg; and Ca, phosphine: the group —P(R)$_2$, wherein each R is independently selected from: hydrogen; C1–C6-alkyl; phenyl; and C1–C6-alkyl-C6H5, phosphine oxide: the group —P(O)R$_2$, wherein R is independently selected from: hydrogen; C1–C6-alkyl; phenyl; and C1–C6-alkyl-C6H5; and amine (to give phosphonamidate) selected from the group: —NR'2, wherein each R' is independently selected from: hydrogen; C1–C6-alkyl; C1–C6-alkyl-C6H5; and phenyl, wherein when both R' are C1–C6-alkyl both R' together may form an —NC3 to an —NC5 heterocyclic ring with any remaining alkyl chain forming an alkyl substituent to the heterocyclic ring.

Unless otherwise specified the following are more preferred group restrictions that may be applied to groups found within compounds disclosed herein:

alkyl: linear and branched C1–C6-alkyl,
alkenyl: C3–C6-alkenyl,
cycloalkyl: C6–C8-cycloalkyl,
alkoxy: C1–C4-alkoxy,
alkylene: selected from the group consisting of: methylene; 1,2-ethylene; 1,3-propylene; butan-2-ol-1,4-diyl; 1,4-butylene; cyclohexane-1,1-diyl; cyclohexan-1,2-diyl; cyclohexan-1,4-diyl; cyclopentane-1,1-diyl; and cyclopentan-1,2-diyl,
aryl: selected from group consisting of: phenyl; biphenyl; naphthalenyl; anthracenyl; and phenanthrenyl,
arylene: selected from the group consisting of: 1,2-phenylene; 1,3-phenylene; 1,4-phenylene; 1,2-naphtalenylene; 1,4-naphtalenylene; 2,3-naphtalenylene and 1-hydroxy-2,6-phenylene,
heteroaryl: selected from the group consisting of: pyridinyl; pyrimidinyl; quinolinyl; pyrazolyl; triazolyl; isoquinolinyl; imidazolyl; and oxazolidinyl, wherein the heteroaryl may be connected to the compound via any atom in the ring of the selected heteroaryl,
heteroarylene: selected from the group consisting of: pyridin-2,3-diyl; pyridin-2,4-diyl; pyridin-2,6-diyl; pyridin-3,5-diyl; quinolin-2,3-diyl; quinolin-2,4-diyl; isoquinolin-1,3-diyl; isoquinolin-1,4-diyl; pyrazol-3,5-diyl; and imidazole-2,4-diyl,
heterocycloalkyl: selected from the group consisting of: pyrrolidinyl; morpholinyl; piperidinyl; piperidinyl; 1,4-piperazinyl; tetrahydrofuranyl; 1,4,7-triazacyclononanyl; 1,4,8,11-tetraazacyclotetradecanyl; 1,4,7,10,13-pentaazacyclopentadecanyl; 1,4,7,10-tetraazacyclododecanyl; and piperazinyl, wherein the heterocycloalkyl may be connected to the compound via any atom in the ring of the selected heterocycloalkyl,
heterocycloalkylene: selected from the group consisting of: piperidin-2,6-ylene; piperidin-4,4-ylidene; 1,4-piperazin-1,4-ylene; 1,4-piperazin-2,3-ylene; 1,4-piperazin-2,6-ylene; tetrahydrothiophen-2,5-ylene; tetrahydrothiophen-3,4-ylene; tetrahydrofuran-2,5-ylene; tetrahydrofuran-3,4-ylene; pyrrolidin-2,5-ylene; pyrrolidin-2,2-ylidene; 1,4,7-triazacyclonon-1,4-ylene; 1,4,7-triazacyclonon-2,3-ylene; 1,4,7-triazacyclonon-2,2-ylidene; 1,4,8,11-tetraazacyclotetradec-1,4-ylene; 1,4,8,11-tetraazacyclotetradec-1,8-ylene; 1,4,8,11-tetraazacyclotetradec-2,3-ylene; 1,4,8,11-tetraazacyclotetradec-2,2-ylidene; 1,4,7,10-tetraazacyclododec-1,4-ylene; 1,4,7,10-tetraazacyclododec-1,7-ylene; 1,4,7,10-tetraazacyclododec-2,3-ylene; 1,4,7,10-tetraazacyclododec-2,2-ylidene; 1,4,7,10,13-pentaazacyclopentadec-1,4-ylene; 1,4,7,10,13-pentaazacyclopentadec-1,7-ylene; 1,4-diaza-7-thia-cyclonon-1,4-ylene; 1,4-diaza-7-thia-cyclonon-2,3-ylene; 1,4-diaza-7-thia-cyclonon-2,2-ylidene; 1,4-diaza-7-oxa-cyclonon-1,4-ylene; 1,4-diaza-7-oxa-cyclonon-2,3-ylene;1,4-diaza-7-oxa-cyclonon-2,2-ylidene; 1,4-dioxan-2,6-ylene; 1,4-dioxan-2,2-ylidene; tetrahydropyran-2,6-ylene; tetrahydropyran-2,5-ylene; and tetrahydropyran-2,2-ylidene, amine: the group —N(R)$_2$, wherein each R is independently selected from: hydrogen; C1–C6-alkyl; and benzyl,
halogen: selected from the group consisting of: F and Cl,
sulphonate: the group —S(O)$_2$OR, wherein R is selected from: hydrogen; C$_1$–C$_6$-alkyl; Na; K; Mg; and Ca,
sulphate: the group —OS(O)$_2$OR, wherein R is selected from: hydrogen; C1–C6-alkyl; Na; K; Mg; and Ca,
sulphone: the group —S(O)$_2$R, wherein R is selected from: hydrogen; C1–C6-alkyl; benzyl and amine selected from the group: —NR'2, wherein each R' is independently selected from: hydrogen; C1–C6-alkyl; and benzyl, carboxylate derivative: the group —C(O)OR, wherein R is selected from hydrogen; Na; K; Mg; Ca; C1–C6-alkyl; and benzyl,
carbonyl derivative: the group: —C(O)R, wherein R is selected from: hydrogen; C1–C6-alkyl; benzyl and amine selected from the group: —NR'2, wherein each R' is independently selected from: hydrogen; C1–C6-alkyl; and benzyl,
phosphonate: the group —P(O)(OR)$_2$, wherein each R is independently selected from: hydrogen; C1–C6-alkyl; benzyl; Na; K; Mg; and Ca,
phosphate: the group —OP(O)(OR)$_2$, wherein each R is independently selected from: hydrogen; C1–C6-alkyl; benzyl; Na; K; Mg; and Ca,
phosphine: the group —P(R)$_2$, wherein each R is independently selected from: hydrogen; C1–C6-alkyl; and benzyl,
phosphine oxide: the group —P(O)R$_2$, wherein R is independently selected from: hydrogen; C1–C6-alkyl; benzyl and amine selected from the group: —NR'2, wherein each R' is independently selected from: hydrogen; C1–C6-alkyl; and benzyl.

The invention will now be further illustrated by way of the following non-limiting examples:

EXAMPLES

[(MeN4Py)FeCl]Cl

The ligand N,N-bis(pyridin-2-yl-methyl)-1,1-bis(pyridin-2-yl)-1-aminoethane (MeN4py) was prepared as described in EP 0 909 809 A2.

The ligand MeN4Py (33.7 g; 88.5 mmoles) was dissolved in dry methanol (500 ml). Small portions of $FeCl_2 \cdot 4H_2O$ (0.95 eq; 16.7 g; 84.0 mmoles) were added, yielding a clear red solution. After addition, the solution was stirred for 30 minutes at room temperature, after which the methanol was removed (rotary-evaporator). The dry solid was ground and 150 ml of ethylacetate was added and the mixture was stirred until a fine red powder was obtained. This powder was washed twice with ethyl acetate, dried in the air and further dried under reduced pressure vacuum at 40° C. El. Anal. Calc. for [Fe(MeN4py)Cl]Cl.2H$_2$O: C 53.03; H 5.16; N 12.89; Cl 13.07; Fe 10.01%. Found C52.29/52.03; H 5.05/5.03; N 12.55/12.61; Cl: 12.73/12.69; Fe: 10.06/10.01%.

1,4,7-triazacyclononane (TACN)

Ligand 1,4,7-triazacyclononane was produced according a modified method used by the team of Prof. K. Wieghardt. In this method the detosylation of the 1,4,7-tris-p-toluenesulphon-1,4,7-triazacyclononanamide was performed in 5 minutes in hot sulphuric acid of 180° C. Once the hot reaction mixture has been cooled to ambient temperatures it was added to ether under vigorous stirring after which the mixture is allowed to settle and separate into different phases. The ethereal solution is decanted and the residue is dissolved in boiling water and concentrated hydrochloric acid added dropwise resulting in the formation of brown crystals. The brown crystals were filtered off and washed with cold hydrochloric acid, ethanol and then ether. The 1,4,7-triazacyclononane trihydrochloride thus produced is then processed further as described by Wieghardt et al. (K. Wieghardt et al, Chem Ber., 112, 2200 (1979)).

1,4,7-triazatricyclo[5.2.1.0$^{410}$]decane (orthoamide)

A mixture of 1,4,7-triazacyclononane (64.3 g, 0.54 mol), orthoformicacidtriethylester (74.8 g) and p-toluolsulphonic acid (20 mmol 4 g) were heated to 150° C. and the resulting ethanol some of the esters are distilled off. After the reaction has been completed the orthoamide was distilled off at a pressure of <80 mbar in the form of a bright yellow volatile oil (b.p. 350 K at 133 Pa), in agreement with literature (T. J. Atkins, J. Am. Chem. Soc., 102, 6365 (1980)).

1-ethyl-1,4,7-triazacyclononane (Et-TACN)

To a solution of orthoamide (0.1 mol 13.92 g) in dry THF ethylbromide (0.1 mol 10.9 g) was slowly added. The resulting suspension was stirred for 2 days at room temperature in a closed flask during which a microcrystalline powder was formed. The microcrystalline powder was removed by filtration and washed with dry THF to yield the bromide salt (hygroscopic). The salt was dissolved in water (80 ml) and heated for 4 hours under reflux after which a solution of sodium hydroxide (16 g) in water (20 ml) was added resulting in the separation of an oil. This mixture was heated under reflux for 20 hours and cooled to ambient temperature. Water was azeotropically removed using toluol (300 ml). The reaction mixture was filtered and the toluol is removed under reduced pressure yielding a bright yellow oil (13.8 g, 89%).

$^1$H-NMR (CDCl$_3$-270 MHz; 300K): 2.59–2.39 (m; 14H); 1.83 (s, 2H); 0.90 ppm (t; 3H); $^{13}$C-NMR: 52.1; 50.7; 46.5; 46.4; 12.4 ppm.

Complex 1

[Fe(1,4-bis(guinolin-2-ylmethyl)-7-ethyl-1,4,7-triazacyclononane)Br](ClO$_4$)

Quinolin-2-ylmethylbromide

A mixture of quinoline (30.0 g, 0.2 mol), N-bromsuccinimide (0.22 mol, 42 g) and a small amount of dibenzoylperoxide as initiator in freshly distilled benzene (300 ml) was irradiated with light. The mixture was cooled below 0° C. and precipitated succinimide removed by filtration. The solvent was then removed under reduced pressure to yield an oil which was added to 5% hydrobromic acid. After addition the mixture was cooled in an ice bath and a saturated solution of sodium carbonate was added slowly until the reaction mixture was pH 7. From the reaction mixture a yellow precipitate was removed by filtration and dried. The yellow precipitate was crystallized from pentane to yield the title compound.

1,4-bis(quinolin-2-ylmethyl)-7-ethyl-1,4,7-triazacyclononane (L$^3$)

To a solution of Et-TACN (3.12 g, 20 mmol) in dry THF (50 ml) was added triethylamine (8 ml, 56.8 mmol) followed by quinolin-2ylmethylbromide (40 mmol 8.96 g), which resulted in a brown solution. After the reaction mixture had been stirred for 3 days the resulting triethylammoniumbromide was removed by filtration. The remaining solvent was removed under reduced pressure yielding a red to brown oil yield 6.6 g (75%)[The by-products (approx. 8%) created by the alkaline hydrolysis of chinolylmethylbromide could not be separated by HPLC, GC or chromatography.

$^1$H-NMR (CDCl$_3$-400 MHz; 300K): 7.92 (d; 2H); 7.89 (d; 2H) 7.62 (d; 2H); 7.52 (d; 2H); 7.50 (m; 2H); 7.34 (m; 2H); 3.87 (S; 4H); 2.94 (m; 4H); 2.88 (m; 4H); 2.68 (m; 4H); 2.53 (q; 2H); 0.92 ppm (t; 3H); $^{13}$C-NMR: 160.2; 147.1; 135.9; 129.0; 128.5; 127.2; 127.0; 125.8; 121.1; 64.9; 55.3; 54.3; 53.6; 51.1; 11.8 ppm. MS (EI): 439 (M$^+$; rel int 20%; 157 (rel int. 40% -quinoline-2carboxaldehyde); 143 (rel int 100%-quinoline).

[Fe (1,4-bis (quinolin-2-ylmethyl)-7-ethyl-1,4,7-triazacyclononane)Br](ClO$_4$)

The following reaction was conducted under argon. To a solution of 1,4-bis(quinolin-2-ylmethyl)-7-ethyl-1,4,7-triazacyclononane (1 mmol, 0.44 g) in 30 ml methanol FeBr$_2$ (1 mmol, 0.22 g) was added and the reaction mixture heated for 2 hours yielding an orange solution. The solution was filtered through a frit to remove undissolved iron bromide. To the resulting filtrate sodium perchlorate was added and the mixture stirred for 2 hours at ambient temperature to yield an orange solid. The solid was filtered and washed with ether to yield the title compound as an air-stable product, yield: 400 mg (59%).

Elem. Anal. Found: C: 48.24; H: 4.63; N: 10.02%. Calc.: C: 49.85; H: 4.89; N: 10.38%

Complex 2

[Fe(1,4-bis(pyridyl-2-methyl)-7-ethyl-1,4,7-triazacyclononane) Cl](ClO4)$_2$

1,4-bis (pyridyl-2-methyl)-7-ethyl-1,4,7-triazacyclononane (L$^4$)

To a suspension of Et-TACN (50 mmol, 7.76 g) in water (120 ml) was added picolylhydrochloride (100 mmol, 16.4 g) yielding a yellow solution. After cooling the reaction mixture in an ice bath NaOH (8.0 g) was added in portions over a period of 5 days such that the pH remained below 9 and the temperature did not exceed 0° C.; the reaction mixture gradually changed from red to brown. The reaction mixture was kept at approximately 4° C. for 24 hrs allowing the formation of a separate organic phase that was separated. The remaining aqueous phase was extracted several times with chloroform. The chloroform extracts were combined and dried over calcium oxide. After filtration of the dried chloroform the solvent was removed under reduced pressure to yield a thick red-brown oil which was contaminated by traces of picolylchloride and by-products of the alkaline hydrolysis of the picolylchlorides (approx. 5%), yield 14.3 g (84%).

$^1$H-NMR (CDCl$_3$-400 MHz; 300K): 8.34 (d; 2H); 7.47 (m; 2H); 7.31 (d; 2H); 6.97 (m; 2H); 3.68 (s; 4H); 2.78(m; 4H); 2.73 (m; 4H); 2.67 (m; 4H); 2.49 (q; 2H); 0.90 ppm (t; 3H); 13C-NMR: 159.8; 145.6; 140.0; 123.0; 121.5; 63.8; 55.8; 55.0; 54.3; 51.7; 12.2 ppm. MS (EI): m/z: 339.

[FeL$^2$Cl](ClO$_4$)$_2$

The iron complex was prepared in analogous manner to the formation of the complex for Complex 1.

Compound 3

[Fe(1,4-bis(pyrazol-1-ylmethyl)-7-ethyl-1,4,7-triazacyclononane)Br](BPh$_4$)

1,4-bis(pyrazol-1-ylmethyl)-7-ethyl-1,4,7-triazacyclononane (L$^5$)

The title compound was synthesised by heating Et-TACN (20 mmol, 3.10 g), pyrazolylmethanol (40 mmol, 3.92) and LIOH (0.4 g) in 50 ml acetonitrile for 20 hours under an argon atmosphere after which the reaction mixture was filtered and the solvent removed under reduced pressure to yield a bright yellow oil, yield 6.3 g (80%) (W. Driessen, Recl. Trav., Chim. Pays-Bas, 101, 441, 1982).

$^1$H-NMR (CDCl$_3$-400 MHz; 300K): 7.43 (d; 4H); 6.21 (s; 2H) 4.93 (s, 4H); 2.83(m; 8H); 2.62 (m; 4H); 2.53 (q; 2H); 0.95 (t, 3H); $^{13}$C-NMR: 139.0; 129.3; 125.9; 72.6; 54.3; 53.5; 52.7; 51.7; 12.3 ppm. MS (EI): m/z: 317.

[Fe (1,4-bis (pyrazol-1-ylmethyl)-7-ethyl-1,4,7-triazacyclononane)(CH$_3$CN)](ClO$_4$)$_2$ The following reaction was conducted under argon atmosphere. To a solution of 1,4-bis(pyrazol-1-ylmethyl)-7-ethyl-1,4,7-triazacyclononane (1 mmol, 0.32 g) in 30 ml acetonitrile iron(II)perchlorate.6H$_2$O (1 mmol, 0.53 g) was added. The solvent was removed slowly by the flow of argon yielding a purple solid. The purple solid was washed with diethylether and dried under reduced pressure, yield: 200 mg (33%). Elem. Anal. Found: C: 34.6; H: 4.8; N: 17.6%. Calc.: C: 35.3; H: 4.9; N: 18.3%

L1: 1,4,7-tris(benzimidazol-2ylmethyl)-1,4,7-triazacyclononane was prepared by procedure A using TACN and chloromethylbenzimidazol-2yl as starting material.

L2: 1,4,7-tris(N-methyl-benzimidazol-2ylmethyl)-1,4,7-triazacyclononane was prepared by procedure B using TACN and N-methylbenzimidazol-2ylcarboxaldehyde as starting material.

L3: 1,4-bis(imidazol-2ylmethyl)-7-ethyl-1,4,7-triazacyclononane was prepared by procedure B using 1-ethyl-TACN and imidazol-2ylcarboxaldehyde L4: 1,4,7-tris(4-bromo-pyrazol-3-ylmethyl)-1,4,7-triazacyclononane was prepared by procedure B using TACN and 4-bromo-pyrazole-3-carboxaldehyde.

L5: 1,4,7-tris(pyrrole-2ylmethyl)-1,4,7-triazacyclononane was prepared according to procedure B using TACN and pyrrole-2-carboxaldehyde as starting material.

Reaction Procedure A (for L1)

To a solution of 2-chloromethylbenzimidazole (4 mmol) and 1 mmol triazacyclononane in 4 ml water at 70° C. was added slowly 0.8 ml 10 NaOH over 10 minutes. The reaction mixture was stirred for an additional 30 minutes at 70° C., after which the reaction mixture was cooled to room temperature. The mixture was extracted with chloroform (3×5 ml) and the organic layer were dried over sodium sulphate, filtered and evaporated under reduced pressure. The material was purified by column chromatography on silica (elutent used was CH$_2$Cl$_2$ which was gradually changed to 10% methanol/CH$_2$Cl$_2$ to 10% methanol/5% NH4OH/CH$_2$Cl$_2$). The products were analysed by ES-MS (positive mode). Yields are typically around 50%.

L1: m/z 520.7 (M+H$^+$)

Reaction Procedure B (for L2–L5)

The general procedure of these ligands is as follows. To a 25 ml glass vial was added either 1,4,7-triazacyclononane or 1-ethyl-1,4,7-triazacyclononane (1 mmol), and aldehyde (4 mmol).

The above-mentioned vial was sealed with a cap and the solution was then shaken for 2 h to allow imine formation. The mixture was treated with NaCNBH$_3$ (3.3 mmol), adjusted to pH 6 with acetic acid and shaken for 38 h. The mixture was quenched with 3 ml of 2 M HCl solution and adjusted to pH>13 with a 7M NaOH solution. The mixture was extracted with 3×10 ml of dichloromethane, dried over sodium sulphate and evaporated under reduced pressure. Yields are typically around 50%. Purities are greater than 90% as established by HPLC/MS.

L2: m/z 562.8 (M+H$^+$)
L3: m/z 318.5 (M+H$^+$)
L4: m/z 608.1 (M+H$^+$)
L5: m/z 367.4 (M+H$^+$)

Bleaching Experiments

In an aqueous solution containing 10 mM carbonate buffer (pH 10) with 0.6 g/l NaLAS (linear alkylbenzene sulphonate) and 10 mM hydrogen peroxide tomato-soya oil stained, curry-soya oil stained or BC-1 (tea)-ex CFT-cloths were added and kept in contact with the solution whilst agitating for 30 minutes at 30° C. Comparative experiments were performed using 20 μM of the ligand and 10 μM of a metal salt (Fe or Co perchlorate), or 10 μM of the metal complex referred to in the table below. The ligand and metal salt were mixed together at a 0.3 mM concentration range in ethanol/water (15/100 v/v) and were left for 30 min at room temperature before being used in the bleach liquor.

After the wash, the cloths were rinsed with water and subsequently dried at 30° C. and the change in colour was measured immediately after drying with a Linotype-Hell scanner (ex Linotype) (t=0 in the table). The tomato stains were left for 24 h in the dark and measured again (t=1 in the table). The change in colour (including bleaching) is expressed as the ΔE value versus white; a lower ΔE value means a cleaner cloth. The measured colour difference (ΔE) between the washed cloth and the unwashed cloth is defined as follows:

$$\Delta E=[(\Delta L)^2+(\Delta a)^2+(\Delta b)^2]^{1/2}$$

wherein ΔL is a measure for the difference in darkness between the washed and unwashed test cloth; Δa and Δb are measures for the difference in redness and yellowness respectively between both cloths. With regard to this colour measurement technique, reference is made to Commission International de l'Eclairage (CIE); Recommendation on Uniform Colour Spaces, colour difference equations, psychometric colour terms, supplement no 2 to CIE Publication, no 15, Colormetry, Bureau Central de la CIE, Paris 1978. The results are shown below in the tables.

Tomato oil (TOL)/pH10 with 0.6 g/l NaLAS and 10 mM $H_2O_2$

|  | (t = 0) | (t = 1) |
|---|---|---|
| Blank | 18 | 18 |
| FeMeN4pyC12 | 5 | 4 |
| L1/Fe | 9 | 2 |
| L2/Fe | 10 | 3 |
| Complex 1 | 6 | 5 |

Curry oil (COL)/pH10 with 0.6 g/l NaLAS and 10 mM $H_2O_2$

|  | (t = 0) |
|---|---|
| Blank | 46 |
| L4/Fe | 38 |
| Complex 2 | 39 |
| Complex 1 | 33 |
| FeMeN4pyC12 | 34 |

BC-1/pH10 with 0.6 g/l NaLAS and 10 mM ($H_2O_2$)

|  | (t = 0) |
|---|---|
| Blank | 13.5 |
| FeMeN4pyC12 | 11.5 |
| L5/Co | 11.0 |
| L3/Fe | 12.0 |
| Complex 2 | 12.0 |
| Complex 3 | 12.0 |

The experiments presented in the tables above show that the iron complexes containing the TACN-derivative ligands as defined herein, as well as the free ligands in combination with iron or cobalt salts, give bleach enhancement using hydrogen peroxide.

Homogeneous Oxidation Experiment

Activation of an alkylhydroxyperoxide by the tacn complexes

To an argon purged solution of Complex 3 (0.1 mM) in acetonitrile, cyclohexane (50 mM) was added followed by 20 mM of tert-butylhydroperoxide (t-BuOOH) (dissolved in di-t-butylether). The reaction mixture was maintained under an argon atmosphere for 30 min followed by the addition of an aqueous solution of sodium sulphate (0.4 M). The iron complex dissolved in the aqueous phase and the products (cyclohexane and cyclohexanone) were analysed by GC. Analyses yielded 0.5–1.5 mM of cyclohexanone +cyclohexanol (5–15 turnovers).

These results show that this complex also activates ROOH in non-aqueous media.

What is claimed is:

1. A bleaching composition comprising an effective amount for bleaching free ligand capable of forming a complex with a transition metal, and at least 1% of a peroxyl species or equivalent source thereof, wherein the complex is of the general formula (A1):

$$[M_aL_kX_n]Y_m \quad (A1)$$

in which:

M represents a metal selected from Mn (II)–(III)–(IV)–(V), Cu(I)–(II)–(III), Fe(II)–(III)–(IV)–(V), Co(I)–(II)–(III), Ti(II)–(III)–(IV), V(II)–(III)–(V), Mo(II)–(III)–(IV)–(V)–(VI) and W(IV)–(V)–(VT);

X represents a coordinating species selected from any mono, bi or tri charged anions and any neutral molecules able to coordinate the metal in a mono, bi or tridentate manner;

Y represents any non-coordinated counter ion;

a represents an integer from 1 to 10;

k represents an integer from 1 to 10;

n represents an integer from 1 to 10;

m represents zero or an integer from 1 to 20; and

L represents a ligand of the general formula (I), or its protonated or deprotonated analogue:

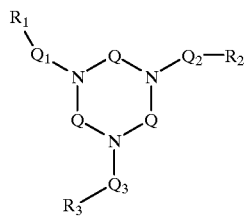

(I)

wherein $R_1$, $R_2$, and $R_3$ independently represent a group selected from hydrogen, hydroxyl, halogen, —NH—C(NH)NH_2, —R and —OR, wherein R=alkyl, alkenyl, cycloalkyl, heterocycloalkyl, aryl, heteroaryl or a carbonyl derivative group, R being optionally substituted by one or more functional groups E;

Q independently represents a group selected from $C_{2-3}$-alkylene optionally substituted by H, benzyl or $C_{1-8}$-alkyl;

$Q_1$, $Q_2$ and $Q_3$ independently represent a group of the formula:

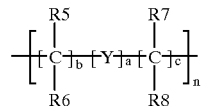

wherein $5 \geq a+b+c \geq 1$; a=0–5; b=0–5; c=0–5; n=1 or 2;

Y independently represents a group selected from —O—, —S—, —SO—, —SO_2—, —C(O)—, arylene, alkylene, heteroarylene, heterocycloalkylene, —(G)P—, —P(O)— and —(G)N—, wherein G is selected from hydrogen, alkyl, aryl, arylalkyl, cycloalkyl, each except hydrogen being optionally substituted by one or more functional groups E;

R5, R6, R7, R8 independently represent a group selected from hydrogen, hydroxyl, halogen, —R and —OR, wherein R represents alkyl, alkenyl, cycloalkyl, heterocycloalkyl, aryl, heteroaryl or a carbonyl derivative group, R being optionally substituted by one or more functional groups E, or R5 together with R6, or R7 together with R8, or both, represent oxygen, or R5 together with R7 and/or independently R6 together with R8, or R5 together with R8 and/or independently R6 together with R7, represent $C_{1-6}$-alkylene optionally substituted by $C_{1-4}$-alkyl, —F, —Cl, —Br or —I; and E independently represents a functional group selected from —F, —Cl, —Br, —I, —OH, —OR', —NH$_2$, —NHR', —N(R')$_2$, —N(R')$_3^+$, —C(O)R', —OC(O)R', —COOH, —COO$^-$(Na$^+$, K$^+$), —COOR', —C(O)NH$_2$, —C(O)NHR', —C(O)N(R')$_2$, heteroaryl, —R', —SR', —SH, —P(R')$_2$, —P(O)(R')$_2$, —P(O)(OH)$_2$, —P(O)(OR')$_2$, —NO$_2$, —SO$_3$H, —SO$_3^-$(Na$^+$, K$^+$), —S(O)$_2$R', —NHC(O)R', and —N(R')C(O)R', wherein R' represents cycloalkyl, aryl, arylalkyl, or alkyl optionally substituted by —F, —Cl, —Br, —I, —NH$_3^+$, —SO$_3$H, —SO$_3^-$(Na$^+$, K$^+$), —COOH, —COO$^-$(Na$^+$, K$^+$), —P(O)(OH)$_2$, or —P(O)(O$^-$(Na$^+$, K$^+$))$_2$, provided that at Least one of R1, R2 and R3 is a coordinating group.

2. A bleaching composition according to claim 1, wherein at least two of $R_1$, $R_2$ and $R_3$ independently represent a coordinating group selected from carboxylate, amido, —NH—C(NH)NH$_2$, hydroxyphenyl, an optionally substituted heterocyclic ring or an optionally substituted heteroaromatic ring selected from pyridine, pyrimidine, pyrazine, pyrazole, imidazole, benzimidazole, quinoline, pyrrole, quinoxaline, triazole, isoquinoline, carbazole, indole, isoindole, oxazole and thiazole.

3. A bleaching composition according to claim 1, wherein at least two of $R_1$, $R_2$, $R_3$ each independently represent a coordinating group selected from optionally substituted pyridin-2-yl, optionally substituted imidazol-2-yl, optionally substituted imidazol-4-yl, optionally substituted pyrazol-1-yl, optionally substituted pyrrol-2-yl, and optionally substituted quinolin-2-yl.

4. A bleaching composition according to claim 1, wherein R5, R6, R7, R8 independently represent a group selected from —H, hydroxy-$C_0$–$C_{20}$-alkyl, halo-$C_0$–$C_{20}$-alkyl, nitroso, formyl-$C_0$–$C_{20}$-alkyl, carboxyl-$C_0$–$C_{20}$-alkyl and esters and salts thereof, carbamoyl-$C_0$–$C_{20}$-alkyl, sulpho-$C_0$–$C_{20}$-alkyl and esters and salts thereof, sulphamoyl-$C_0$–$C_{20}$-alkyl, amino-$C_0$–$C_{20}$-alkyl, aryl-$C_0$–$C_{20}$-alkyl, $C_0$–$C_{20}$-alkyl, alkoxy-$C_0$–$C_8$-alkyl, carbonyl-$C_0$–$C_6$-alkoxy, and $C_0$–$C_{20}$-alkylamide.

5. A bleaching composition according to claim 1, wherein $Q_1$, $Q_2$ and $Q_3$ are defined such that a=b=0, c=1,2,3 or 4 and n=1.

6. A bleaching composition according to claim 1, wherein $Q_1$, $Q_2$ and $Q_3$ independently represent a group selected from —CH$_2$— and —CH$_2$CH$_2$—.

7. A bleaching composition according to claim 1, wherein Q represents a group selected from —CH$_2$CH$_2$— and —CH$_2$CH$_2$CH$_2$—.

8. A bleaching composition according to claim 1, wherein the ligand L is of the general formula (II):

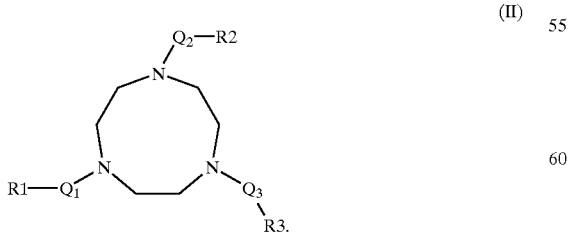

(II)

9. A bleaching composition according to claim 8, wherein R1, R2, R3 each independently represent a coordinating group selected from carboxylate, amido, —NH—C(NH)NH$_2$, hydroxyphenyl, an optionally substituted heterocyclic ring or an optionally substituted heteroaromatic ring selected from pyridine, pyrimidine, pyrazine, pyrazole, imidazole, benzimidazole, quinoline, quinoxaline, triazole, pyrrole, isoquinoline, carbazole, indole, isoindole, oxazole and thiazole.

10. A bleaching composition according to claim 9, wherein

R1, R2, R3 each independently represent a coordinating group selected from optionally substituted pyridin-2-yl, optionally substituted imidazol-2-yl, optionally substituted imidazol-4-yl, optionally substituted pyrazol-1-yl, optionally substituted pyrrol-2-yl, and optionally substituted quinolin-2-yl.

11. A bleaching composition according to claim 8, wherein two of R1, R2, R3 each independently represent a coordinating group selected from carboxylate, amido, —NH—C(NH)NH$_2$, hydroxyphenol, an optionally substituted heterocyclic ring or an optionally substituted heteroaromatic ring selected from pyridine, pyrimidine, pyrazine, pyrazole, imidazole, benzimidazole, quinoline, pyrrole, quinoxaline, triazole, isoquinoline, carbazole, indole, isoindole, oxazole and thiazole; and one of R1, R2, R3 represents a group selected from hydrogen, $C_{1-20}$ optionally substituted alkyl, $C_{1-20}$ optionally substituted arylalkyl, aryl, and $C_{1-20}$ optionally substituted NR$_3^+$ (wherein R=$C_{1-8}$-alkyl).

12. A bleaching composition according to claim 11, wherein two of R1, R2, R3 each independently represent a coordinating group selected from optionally substituted pyridin-2-yl, optionally substituted imidazol-2-yl, optionally substituted imidazol-4-yl, optionally substituted pyrazol-1-yl, optionally substituted pyrrol-2-yl, and optionally substituted quinolin-2-yl; and one of R1, R2, R3 represents a group selected from hydrogen, $C_{1-10}$ optionally substituted alkyl, $C_{1-5}$-furanyl, $C_{1-5}$ optionally substituted benzylalkyl, benzyl, $C_{1-5}$ optionally substituted alkoxy, and $C_{1-20}$ optionally substituted N$^+$Me$_3$.

13. A bleaching composition according to claim 1, wherein the composition comprises a mixture of the ligand L and a metal salt MX$_n$ in which n=1–5.

14. A bleaching composition according to claim 1, wherein L represents a ligand selected from:

1,4,7-Tris(pyrazol-1-ylmethyl)-1,4,7-triazacyclononane; 1,4,7-Tris(pyrazol-1-ylmethyl)-1,4,7-triazacyclononane; 1-ethyl-4,7-bis(quinolin-2-ylmethyl)-1,4,7-triazacyclononane; 1,4-bis(pyridin-2-ylmethyl)-7-ethyl-1,4,7-triazacyclononane; 1,4-bis(pyrazol-2-ylmethyl)-7-ethyl-1,4,7-triazacyclononane; 1,4,7-Tris(benzimidazol-2-ylmethyl)-1,4,7-triazacyclononane; 1,4,7-tris(N-methyl-benzimidazol-2ylmethyl)-1,4,7-triazacyclononane; 1,4-bis(imidazol-2ylmethyl)-7-ethyl-1,4,7-triazacyclononane; 1,4,7-tris(4-bromo-pyrazol-3ylmethyl)-1,4,7-triazacyclononane; 1,4,7-tris(pyrrole-2ylmethyl)-1,4,7-triazacyclononane; 1,4-bis(quinolin-2-ylmethyl)-7-ethyl-1,4,7-triazacyclononane; 1,4-bis(pyrazol-1-ylmethyl)-7-ethyl-1,4,7-triazacyclononane; 1,4-bis(3,5-dimethylpyrazol-1-ylmethyl)-7-ethyl-1,4,7-triazacyclononane; 1,4-bis(N-methylimidazol-2-ylmethyl)-7-ethyl-1,4,7-triazacyclononane; 1,4,7-tris(quinolin-2-ylmethyl)-1,4,7-triazacyclononane; 1,4-bis (N-isopropylacetamido)-7-ethyl-1,4,7-triazacyclononane; and, 1,4-bis(N-methylacetamido)-7-ethyl-1,4,7-triazacyclononane.

15. A bleaching composition according to claim 1, wherein the peroxyl source is present in the range of about 5–35%.

16. A bleaching composition according to claim 1, wherein the composition comprises a preformed complex of the ligand and a transition metal.

17. A bleaching composition according to claim 16, wherein the transition metal is selected from the group consisting of: Fe; Co; Mn and Cu.

18. A bleaching composition according to claim 1, wherein the ligand is present as a free ligand that complexes with a transition metal selected from the source of: transition metal present in the bleaching composition, adventitious transition metal ions present in tap water, transition metal ions present in a stain.

19. A bleaching composition according to claim 1, comprising a builder.

20. A method of bleaching a substrate comprising: applying to the substrate, in an aqueous medium, from 1 μM to 50 mM by weight of the medium of a free ligand capable of complexing with a transition metal, and a peroxyl species or equivalent source thereof present in an effective amount for bleaching the substrate, wherein the complex is of the general formula (A1):

[M$_a$L$_k$X$_n$]Y$_m$ (A1)

in which:

M represents a metal selected from Mn (II)–(III)–(IV)–(V), Cu(I)–(II)–(III), Fe(II)–(III)–(IV)–(V), Co(I)–(II)–(III), Ti(II)–(III)–(IV), V(II)–(III)–(IV)–(V), Mo(II)–(III)–(IV)–(V)–(VI) and W(IV)–(V)–(IV);

X represents a coordinating species selected from any mono, bi or tri charged anions and any neutral molecules able to coordinate the metal in a mono, bi or tridentate manner;

Y represents any non-coordinated counter ion;

a represents an integer from 1 to 10;

k represents an integer from 1 to 10;

n represents an integer from 1 to 10;

m represents zero or an integer from 1 to 20; and

L represents a ligand of the general formula (I), or its protonated or deprotonated analogue:

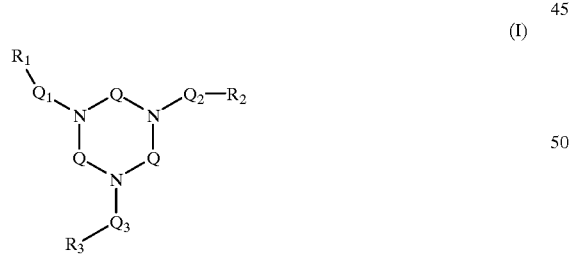

(I)

wherein

R$_1$, R$_2$, and R$_3$ independently represent a group selected from hydrogen, hydroxyl, halogen, —NH—C(NH)NH$_2$, —R and —OR, wherein R=alkyl, alkenyl, cycloalkyl, heterocycloalkyl, aryl, heteroaryl or a carbonyl derivative group, R being optionally substituted by one or more functional groups E;

Q independently represents a group selected from C$_{2-3}$-alkylene optionally substituted by H, benzyl or C$_{1-8}$-alkyl;

Q$_1$, Q$_2$ and Q$_2$ independently represent a group of the formula:

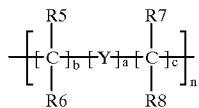

wherein

5≧a+b+c≧1; a=0–5; b=0–5; c=0–5; n=1 or 2;

Y independently represents a group selected from —O—, —S—, —SO—, —SO$_2$—, —C(O)—, arylene, alkylene, heteroarylene, heterocycloalkylene, —(G)P—, —P(O)— and —(G)N—, wherein G is selected from hydrogen, alkyl, aryl, arylalkyl, cycloalkyl, each except hydrogen being optionally substituted by one or more functional groups E;

R5, R6, R7, R8 independently represent a group selected from hydrogen, hydroxyl, halogen, —R and —OR, wherein R represents alkyl, alkenyl, cycloalkyl, heterocycloalkyl, aryl, heteroaryl or a carbonyl derivative group, R being optionally substituted by one or more functional groups E, or R5 together with R6, or R7 together with R8, or both, represent oxygen, or R5 together with R7 and/or independently R6 together with R8, or R5 together with R8 and/or independently R6 together with R7, represent C$_{1-6}$-alkylene optionally substituted by C$_{1-4}$alkyl, —F, —Cl, —Br or —I; and E independently represents a functional group selected from —F, —Cl, —Br, —I, —OH, —OR', —NH$_2$, —NHR', —N(R')$_2$, —N(R')$_3$$^+$, —C(O)R', —OC(O)R', —COOH, —COO$^-$(Na$^+$, K$^+$), —COOR', —C(O)NH$_2$, —C(O)NHR', —C(O)N(R')$_2$, heteroaryl, —R', —SR', —SH, —P(R')$_2$, —P(O)(R')$_2$, —P(O)(OH)$_2$, —P(O)(OR')$_2$, —NO$_2$, —SO$_3$H, —SO$_3$$^-$(Na$^+$, K$^+$), —S(O)$_2$R', —NHC(O)R', and —N(R')C(O)R', wherein R' represents cycloalkyl, aryl, arylalkyl, or alkyl optionally substituted by —F, —Cl, —Br, —I, —NH$_3$$^+$, —SO$_3$H, —SO$_3$$^-$(Na$^+$, K$^+$), —COOH, —COO$^-$(Na$^+$, K$^+$), —P(O)(OH)$_2$, or —P(O)(O$^-$(Na$^+$, K$^+$))$_2$, provided that at least one of R$_1$, R$_2$ and R$_3$ is a coordinating group.

21. A ligand selected from the group consisting of 1,4,7-tris(benzimidazol-2-ylmethyl)-1,4,7-triazacyclononane; 1,4,7-tris(N-methyl-benzimidazol-2ylmethyl)-1,4,7-triazacyclononane; 1,4-bis(imidazol-2ylmethyl)-7-ethyl-1,4,7-triazacyclononane; 1,4,7-tris(4-bromo-pyrazol-3ylmethyl)-1,4,7-triazacyclononane; and, 1,4,7-tris(pyrrole-2ylmethyl)-1,4,7-triazacyclononane.

22. A method according to claim 20 further comprising an effective amount for cleaning of an anionic surfactant.

* * * * *